United States Patent
Govari et al.

(10) Patent No.: US 7,536,218 B2
(45) Date of Patent: May 19, 2009

(54) HYBRID MAGNETIC-BASED AND IMPEDANCE-BASED POSITION SENSING

(75) Inventors: Assaf Govari, Haifa (IL); Andres Claudio Altmann, Haifa (IL); Yitzhack Schwartz, Haifa (IL); Yaron Ephrath, Karkur (IL)

(73) Assignee: Biosense Webster, Inc., Diamond Bar, CA (US)

( * ) Notice: Subject to any disclaimer, the term of this patent is extended or adjusted under 35 U.S.C. 154(b) by 219 days.

(21) Appl. No.: 11/182,272

(22) Filed: Jul. 15, 2005

(65) Prior Publication Data

US 2007/0016007 A1 Jan. 18, 2007

(51) Int. Cl.
*A61B 5/05* (2006.01)

(52) U.S. Cl. ...................... 600/424; 600/547

(58) Field of Classification Search ......... 600/421–424, 600/374, 393, 547, 427, 506–511, 481, 411, 600/466, 467, 435; 128/899, 898; 606/41
See application file for complete search history.

(56) References Cited

U.S. PATENT DOCUMENTS

| | | | | |
|---|---|---|---|---|
| 4,690,152 A * | 9/1987 | Juncosa | | 600/547 |
| 5,391,199 A | 2/1995 | Ben-Haim | | |
| 5,443,489 A | 8/1995 | Ben-Haim | | |
| 5,558,091 A | 9/1996 | Acker et al. | | |
| 5,899,860 A | 5/1999 | Pfeiffer et al. | | |
| 5,944,022 A | 8/1999 | Nardella et al. | | |
| 5,983,126 A | 11/1999 | Wittkampf | | |
| 6,050,267 A * | 4/2000 | Nardella et al. | | 128/899 |
| 6,172,499 B1 | 1/2001 | Ashe | | |
| 6,177,792 B1 | 1/2001 | Govari et al. | | |
| 6,456,864 B1 | 9/2002 | Swanson et al. | | |
| 6,574,498 B1 | 6/2003 | Gilboa | | |
| 6,690,963 B2 | 2/2004 | Ben-Haim et al. | | |
| 6,738,673 B2 * | 5/2004 | Desai | | 607/116 |
| 6,788,967 B2 | 9/2004 | Ben-Haim et al. | | |
| 6,826,420 B1 * | 11/2004 | Beatty et al. | | 600/374 |
| 6,947,785 B1 * | 9/2005 | Beatty et al. | | 600/427 |
| 7,300,438 B2 * | 11/2007 | Falwell et al. | | 606/41 |
| 2002/0065455 A1 * | 5/2002 | Ben-Haim et al. | | 600/407 |
| 2002/0165448 A1 * | 11/2002 | Ben-Haim et al. | | 600/424 |
| 2003/0078509 A1 | 4/2003 | Panescu | | |
| 2004/0181139 A1 | 9/2004 | Falwell | | |
| 2007/0038078 A1 * | 2/2007 | Osadchy | | 600/424 |

OTHER PUBLICATIONS

EPO Search Report 06253717.0-1265, dated Mar. 29, 2007.
U.S. Appl. No. 10/629,661, Biosense Webster, Inc.
U.S. Appl. No. 11/030,934, Biosense Webster, Inc.

* cited by examiner

*Primary Examiner*—Eric F Winakur
*Assistant Examiner*—Lawrence N Laryea
(74) *Attorney, Agent, or Firm*—Louis J. Capezzuto

(57) ABSTRACT

A position sensing system includes a probe adapted to be introduced into a body cavity of a subject. The probe includes a magnetic field transducer and at least one probe electrodes. A control unit is configured to measure position coordinates of the probe using the magnetic field transducer. The control unit also measures an impedance between the at least one probe electrodes and one or more points on a body surface of the subject. Using the measured position coordinates, the control unit calibrates the measured impedance.

24 Claims, 6 Drawing Sheets

FIG. 6A
FIG. 6B
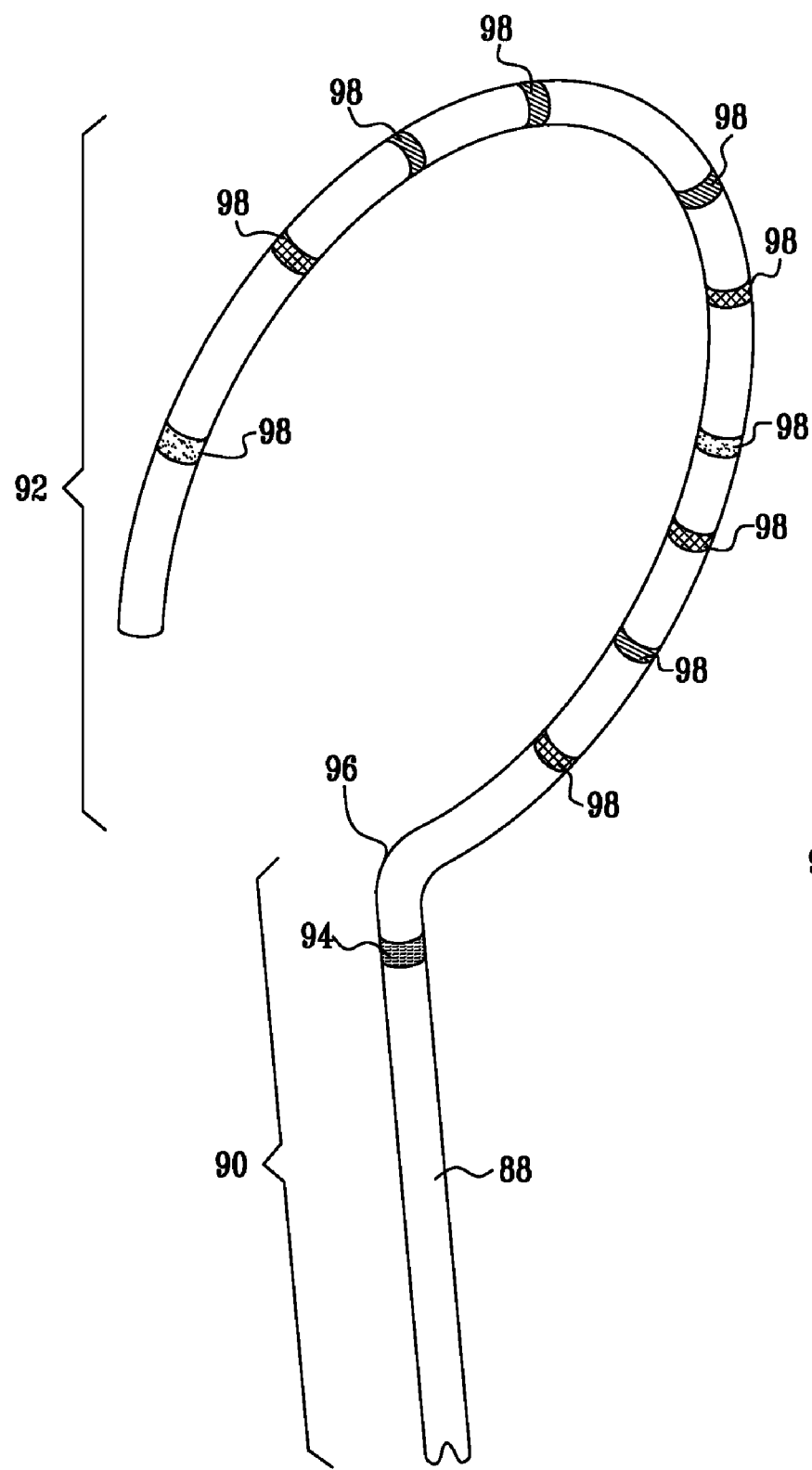
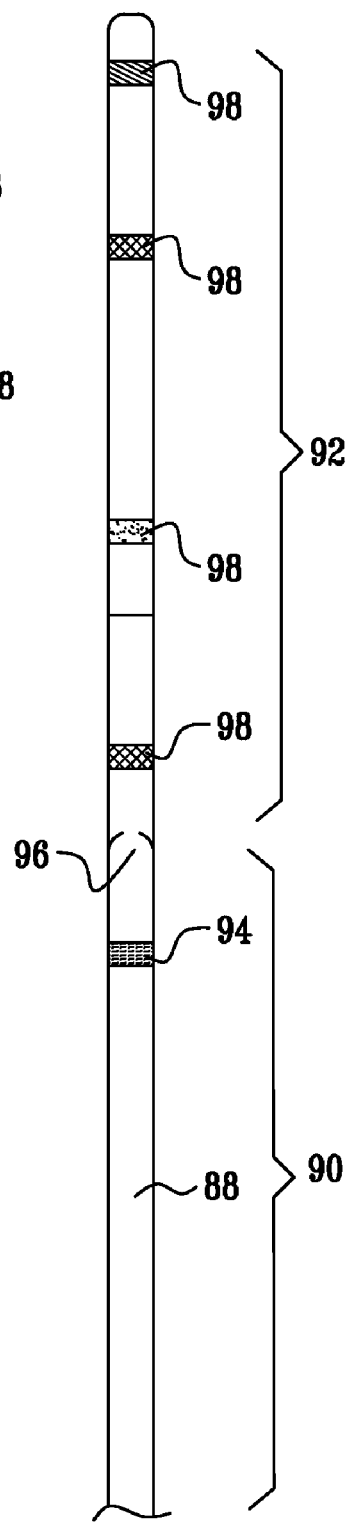

FIG. 6C
FIG. 6D
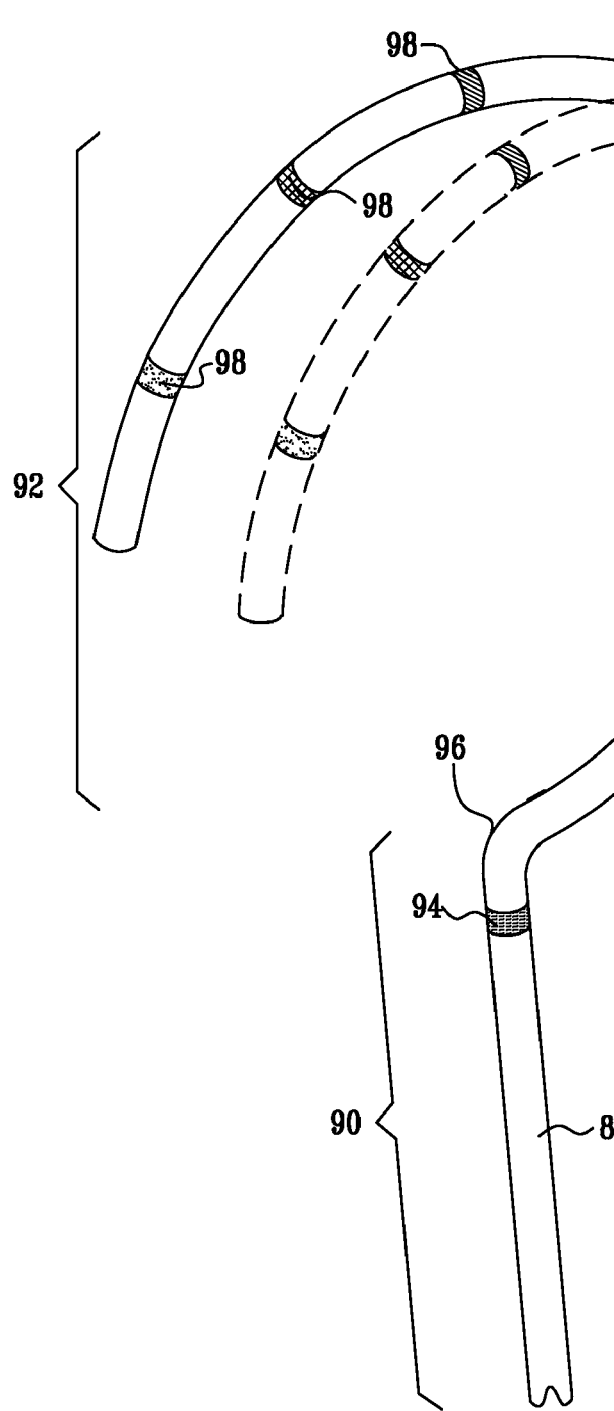
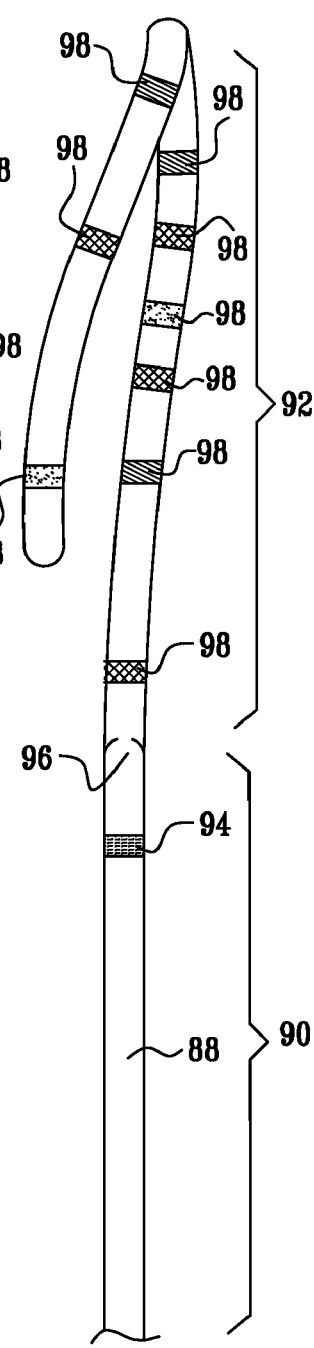

HYBRID MAGNETIC-BASED AND IMPEDANCE-BASED POSITION SENSING

FIELD OF THE INVENTION

The present invention relates generally to sensing the position of an object placed within a living body, and specifically to providing an accurate reference for impedance-based position sensors.

BACKGROUND OF THE INVENTION

Tracking the position of intrabody objects, such as sensors, tubes, catheters, dispensing devices, and implants, is required for many medical procedures. Well-established, highly accurate systems for determining the position of an intrabody object have been developed based on magnetic field sensing. These systems utilize sensors affixed to the intrabody object to measure the relative strengths of externally-generated magnetic fields and to derive from these measurements the position of the object. Methods for magnetic-based position sensing are disclosed, for example, in U.S. Pat. Nos. 5,391,199, 5,443,489, and 6,788,967 to Ben-Haim, in U.S. Pat. No. 6,690,963 to Ben-Haim, et al., in U.S. Pat. No. 5,558,091 to Acker et al., in U.S. Pat. No. 6,172,499 to Ashe, and in U.S. Pat. No. 6,177,792 to Govari, all of whose disclosures are incorporated herein by reference.

Position sensing systems have also been developed which utilize impedance-based measurements. In such systems, impedance is measured between electrodes affixed to the intrabody object and electrodes placed on the body surface. The systems then derive the position of the intrabody object from the impedance measurements. Methods for impedance-based position sensing are disclosed, for example, in U.S. Pat. No. 5,983,126 to Wittkampf, in U.S. Pat. No. 6,456,864 to Swanson, and in U.S. Pat. No. 5,944,022 to Nardella, all of whose disclosures are incorporated herein by reference.

Impedance-based position sensing is generally less expensive to implement than magnetic field position sensing. Many standard catheters, such as those used for electrophysiological mapping and ablation, already incorporate electrodes that can be utilized for impedance measurements. However, due in part to the non-linear impedance of the body, impedance-based position sensing is not as accurate as magnetic-based methods.

U.S. Pat. No. 6,574,498 to Gilboa, whose disclosure is incorporated herein by reference, describes a method of intrabody navigation that relies on an electromagnetic technique to determine the position and orientation of the patient relative to an imaging device, while using another technique, such as the ultrasonic or electrical impedance sensing, to determine the position and orientation of a probe relative to the patient's body. The method includes determining a position and an orientation of the probe relative to a primary coordinate system and to a secondary coordinate system, and determining a transformation from the secondary coordinate system to the primary coordinate system.

U.S. Pat. No. 5,899,860 to Pfeiffer, et al., whose disclosure is incorporated herein by reference, describes a method for determining the position of a catheter inside the body of a patient. A correction function is determined by having a catheter perform a known movement inside a body cavity at the same time as the position of the catheter is determined from position signals sent between the catheter and a remote position location. Subsequent catheter positions, derived from received location signals, are corrected according to the correction function.

Magnetic-based position sensing systems currently available include proprietary products such as the CARTO™ EP Navigation and Ablation System and the LASSO™ Circular Mapping Catheter from Biosense-Webster (Diamond Bar, Calif.).

SUMMARY OF THE INVENTION

Embodiments of the present invention provide hybrid position sensing systems and methods, which combine magnetic and electrical position sensing techniques. In these systems, a magnetic position sensor provides an accurate position reference for calibrating less accurate, electrical impedance-based measurements. For this purpose, a hybrid probe, such as a catheter, comprising a magnetic position sensor and one or more electrodes is used to correlate the magnetic position measurements with the impedance-based measurements. Systems of this sort alleviate the need for multiple magnetic position sensors, and thus benefit from both the high accuracy of magnetic position sensing and the low cost of impedance-based sensing.

In some embodiments of the present invention, the hybrid catheter is positioned in a body cavity, such as a heart chamber. Externally-applied magnetic fields are measured by the magnetic field sensor, and accurate position coordinates of the catheter are derived. Currents or voltages from body-surface electrodes are also applied, and impedances between the body-surface electrodes and the catheter electrodes are measured. The dual position measurements are repeated at multiple locations within the body cavity in order to generate a calibration map, correlating the impedance measurements with position coordinates ascertained by the magnetic field sensor.

Subsequently, additional catheters having diagnostic or therapeutic functions may be introduced into the body cavity. The additional catheters may be introduced simultaneously with the hybrid catheter and/or following removal of the hybrid catheter from the body. These additional catheters also incorporate electrodes similar to those of the hybrid catheter, but need not include magnetic field sensors. Impedance measurements taken from the electrodes on the additional catheters are correlated with the calibration map in order to determine accurate position coordinates of these additional catheters.

In other embodiments of the present invention, the hybrid catheter comprises a deformable portion, such as a lasso at the distal end of the catheter, with electrodes on the deformable portion. Both magnetic and impedance-based measurements are taken while the catheter is held steady, in a known configuration (i.e., when the shape is undeformed). In this configuration, the position of each electrode is known a priori relative to the magnetic sensor. Positions of the electrodes are therefore known on the basis of the magnetic position measurements, and the known positions may be used to calibrate impedance measurements taken at each electrode. When the catheter is subsequently deformed during a medical procedure, the small deflections in the electrode positions from their calibrated positions can be measured relatively accurately by impedance-based methods.

There is therefore provided, in accordance with an embodiment of the present invention, a method for position sensing, including:

introducing a probe including a magnetic field transducer and at least one probe electrode into a body cavity of a subject;

measuring position coordinates of the probe at a location in the body cavity using the magnetic field transducer;

measuring an impedance between the at least one probe electrode and one or more points on a body surface of the subject; and calibrating the measured impedance using the measured position coordinates.

Typically, the magnetic field transducer includes one or more coils.

Typically, measuring the position coordinates of the probe includes generating an external magnetic field and measuring signals induced in the magnetic field transducer due to the external magnetic field.

In some embodiments, measuring the position coordinates includes driving the magnetic field transducer to generate a magnetic field and measuring signals induced in an external magnetic field sensor due to the magnetic field.

In further embodiments, measuring the impedance includes driving an electrical current through the body between the at least one probe electrode and one or more body surface electrodes and measuring the impedance responsively to the current. Typically, driving the electrical current through the body includes maintaining a constant voltage between the at least one probe electrode and the one or more body surface electrodes, and measuring the impedance includes measuring the current at the constant voltage. In still further embodiments, driving the electrical current through the body includes maintaining a constant current between the at least one probe electrode and the one or more body surface electrodes, and measuring the impedance includes measuring a voltage between the at least one probe electrode and the one or more body surface electrodes.

Typically, measuring the impedance includes applying a voltage across at least one pair of body surface electrodes and measuring a voltage drop at the at least one probe electrode.

Typically, measuring the position coordinates includes determining the position coordinates using the magnetic transducer at a plurality of locations in the body cavity, and measuring the impedance includes determining the impedance at the plurality of the locations, and calibrating the measured impedance includes generating a calibration map using the position coordinates and the impedance determined at the plurality of the locations. In further embodiments, the probe used to generate the calibration map is a first probe, and the method further includes:

introducing into the body cavity a second probe including at least one second probe electrode, and measuring the impedance between the at least one second probe electrode and the one or more points on the body surface, and determining second position coordinates of the second probe by calibrating the impedance measured with respect to the second probe electrode using the calibration map.

Typically, the probe includes a base section, where the magnetic field transducer is located and, and a deformable section, where the at least one probe electrode is located, the deformable section having a known shape when undeformed, and the calibrating the measured impedance includes determining a deflection of the deformable section relative to the base section. In further embodiments, determining the displacement includes measuring a first impedance when the deformable section is undeformed, and measuring a second impedance when the deformable section is deflected, and comparing the second impedance to the first impedance in order to determine the deflection.

There is also provided, in accordance with an embodiment of the present invention, a position sensing system, including:

a probe including a magnetic field transducer and at least one probe electrode and adapted to be introduced into a body cavity of a subject; and a control unit configured to measure position coordinates of the probe using the magnetic field transducer, and to measure an impedance between the at least one probe electrode and one or more points on a body surface of the subject, and to calibrate the measured impedance using the measured position coordinates.

In some embodiments, the system includes an external magnetic field generator adapted to generate an external magnetic field, which causes the magnetic field transducer to generate a position signal, and the control unit is configured to receive and process the position signal so as to measure the position coordinates of the probe.

Typically, the magnetic field transducer is adapted to generate a magnetic field, and the system further includes an external magnetic field sensor adapted, responsively to the magnetic field, to generate a position signal. The control unit is configured to receive and process the position signal so as to measure the position coordinates of the probe.

In some embodiments, the control unit is configured to drive an electrical current between the at least one probe electrode and body surface electrodes at the one or more points, and to measure the impedance responsively to the current. In further embodiments, the control unit is configured to maintain a constant voltage between the at least one probe electrode and the body surface electrodes, and to measure the current at the constant voltage. In still further embodiments, the control unit is configured to maintain a constant current between the at least one probe electrode and the body surface electrodes, and to measure the voltage between the at least one probe electrode and the body surface electrodes.

Typically, the control unit is configured to apply a voltage across at least one pair of body surface electrodes at the one or more points and to measure the impedance by sensing a voltage drop at the at least one probe electrode.

In some embodiments, the control unit is configured to determine the position coordinates using the magnetic transducer at a plurality of locations in the body cavity and to determine the impedance at the plurality of the locations, and to generate a calibration map determining the impedance at the plurality of the locations. Typically, the probe used to generate the calibration map is a first probe, and the system further includes a second probe, including at least one second probe electrode and adapted to be introduced into the body cavity, and the control unit is configured to measure the impedance between at least one second probe electrode and the one or more points on the body surface and to determine second position coordinates of the second probe by calibrating the impedance measured with respect to the second probe electrode using the calibration map.

Additionally or alternatively, the probe includes a deformable section where the at least one probe electrode is located, and a base section, where the magnetic field transducer is located, the deformable section having a known shape when undeformed, and the control unit is configured to calibrate the measured impedance so as to determine a deflection of the deformable section relative to the base section. In further embodiments, the control unit is configured to measure a first impedance when the deformable section is undeformed, and to measure a second impedance when the deformable section is deflected, and to compare the second impedance to the first impedance so as to determine the deflection of the probe.

The present invention will be more fully understood from the following detailed description of the embodiments thereof, taken together with the drawings in which:

BRIEF DESCRIPTION OF THE DRAWINGS

FIGS. 6A-6D are schematic, pictorial illustrations of a hybrid catheter, in accordance with another embodiment of the present invention.

DETAILED DESCRIPTION OF EMBODIMENTS

Figure 1:
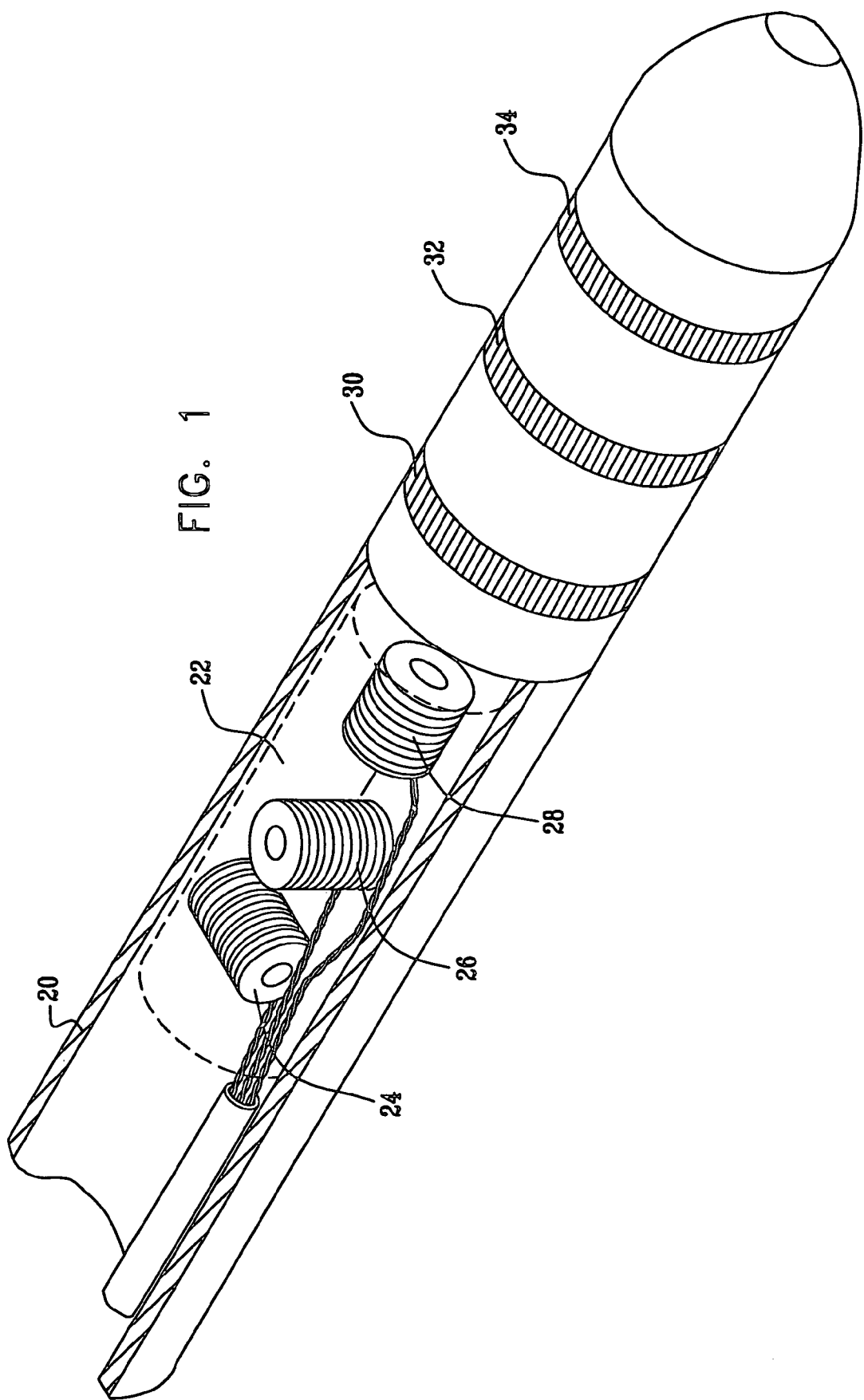
FIG. 1 is a schematic detail view showing the distal end of a hybrid catheter comprising a magnetic field position sensor and multiple electrodes, in accordance with an embodiment of the present invention.

FIG. 1 is a schematic detail view showing the distal end of a hybrid catheter 20, comprising a magnetic field position sensor 22 and multiple catheter electrodes 30, 32, and 34, in accordance with an embodiment of the present invention.

Magnetic field sensor 22 comprises three orthogonal coils 24, 26, and 28, which may be used to determine the coordinates of catheter 20 in six position and orientation dimensions, as described in the patents cited in the Background of the Invention. Alternatively, magnetic field sensor 22 may comprise one or two coils or a greater number of coils, or magnetic field sensors other than coils, such as Hall effect devices or other antennae. In the context of the present patent application and in the claims, such coils and other sensors are referred to generically as magnetic field transducers, and may generally be used either to sense magnetic fields or to generate magnetic fields.

Electrodes 30, 32, and 34 may be of any suitable shape and size, and may be used for other purposes, as well, such as for electrophysiological sensing or ablation.

In an embodiment of the present invention, the distal end of catheter 20 may be flexible, such that the positions of one or more of electrodes 30, 32, and 34 may be deflected relative to the position of magnetic field sensor 22.

Figure 2:
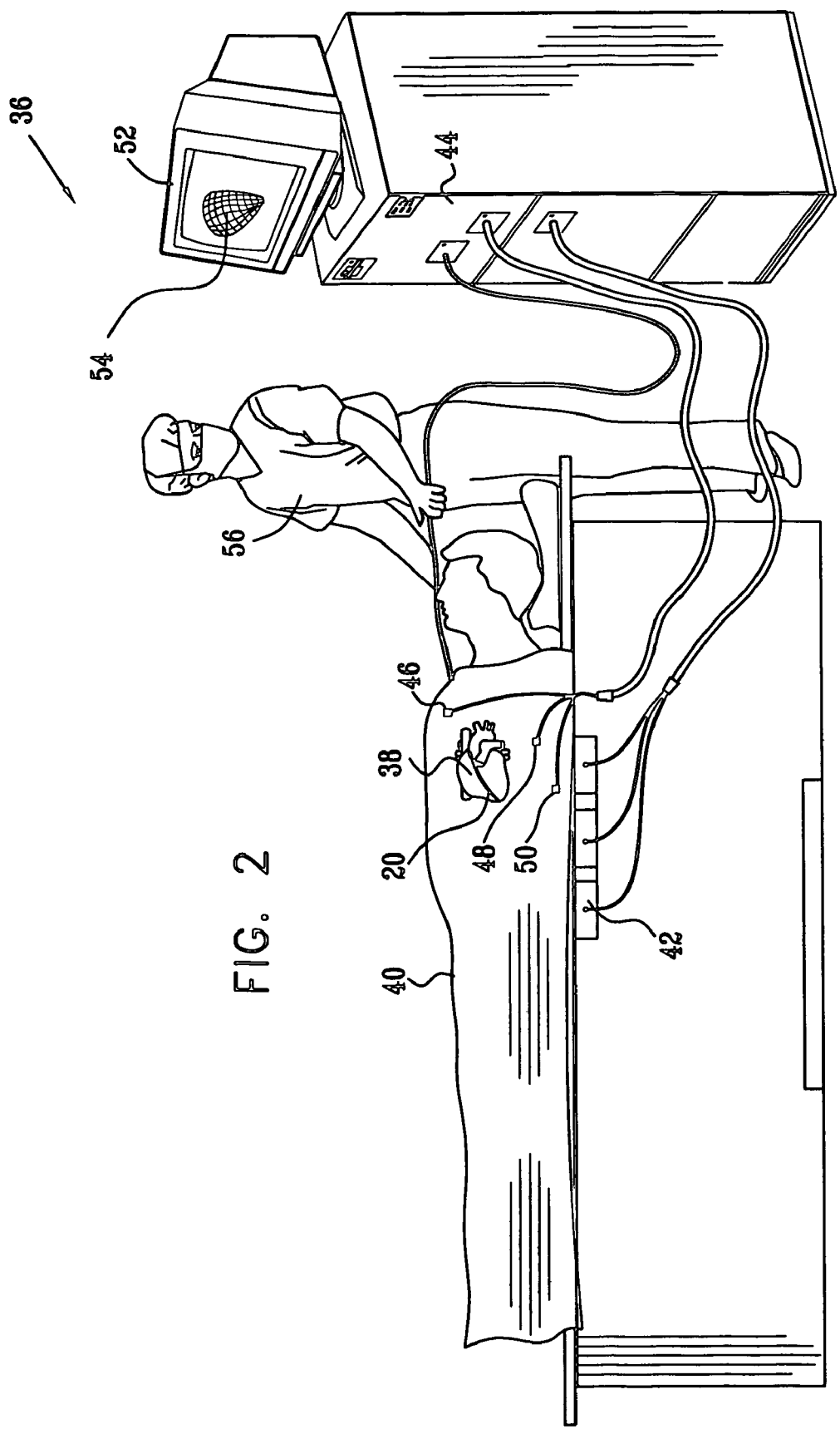
FIG. 2 is a schematic, pictorial illustration of a position sensing system utilizing a hybrid catheter, in accordance with an embodiment of the present invention.

FIG. 2 is a schematic, pictorial illustration of a position sensing system 36, utilizing hybrid catheter 20, in accordance with an embodiment of the present invention. System 36 may be used to determine the position and shape of catheter 20, and may also be used to generate a calibration map from measurements made by catheter 20, as described hereinbelow. The calibration map may be used for subsequent position sensing of additional invasive medical devices that comprise electrodes but may lack magnetic field sensors.

In this embodiment, catheter 20 is used in an invasive procedure within a chamber of a heart 38 of a subject 40. Alternatively, position system 36 may be used with hybrid probes like catheter 20 in other body cavities. Subject 40 is placed in a magnetic field generated, for example, by situating under the subject a pad containing magnetic field generator coils 42. The magnetic fields generated by coils 42 generate electrical signals in coils 24, 26 and 28 of sensor 22, indicative of their position and orientation in the magnetic fields. These signals are conveyed to a control unit 44, which analyzes the signals so as to determine the coordinates of catheter 20. Alternatively, the coils in magnetic field sensor 22 may be driven to generate magnetic fields, which are detected by coils 42.

Control unit 44 includes a processor, typically a computer with appropriate signal processing circuits. The processor is coupled to drive console 52, which may provide a visual display 54 of the location of catheter 20.

Electrodes 30, 32, and 34 are connected by wires through the insertion tube of catheter 20 to impedance measurement circuitry in control unit 44. The control unit is connected by wires to body surface electrodes, which typically comprise adhesive skin patches 46, 48, and 50. Patches 46, 48, and 50 may be placed at any convenient locations on the body surface in the vicinity of the probe. In alternative embodiments of the invention, the electrodes on the body surface may vary in number and may take other forms, such as subcutaneous probes or a handheld device operated by a medical professional 56.

In an embodiment of the present invention, impedances between the surface patches and electrodes 30, 32, and 34 are measured according to methods described in U.S. patent application Ser. No. 11/030,934, filed Jan. 7, 2005, entitled "Current-based Impedance Measurement," to Govari, et al., which is assigned to the assignee of the present invention and which is incorporated herein by reference. Control unit 44 drives currents through one or more electric circuits, each of which comprises a catheter electrode, a respective body surface electrode, and the intervening body tissue. By Ohm's law, the impedance between the electrode and patch in each circuit equals the voltage between the electrodes, divided by the current that flows through the circuit.

In alternative embodiments of the invention, voltages may be applied across pairs of body surface electrodes, as described by the abovementioned U.S. Pat. No. 5,983,126 to Wittkampf. The respective voltage drops at the catheter electrodes are measured to determine the relative impedances.

Typically, system 20 includes other elements, which are not shown in the figures for the sake of simplicity. For example, system 20 may include an ECG monitor, coupled to receive signals from one or more body surface electrodes, so as to provide an ECG synchronization signal to control unit 44. The system may also include a reference position sensor, either on an externally-applied reference patch attached to the exterior of the subject's body, or on an internally-placed catheter, inserted into heart 38 and maintained in a fixed position relative to the heart. By comparing the position of catheter 20 to that of the reference catheter, the coordinates of catheter 20 are accurately determined relative to the heart, irrespective of heart motion. Alternatively, other suitable methods may be used to compensate for heart motion.

Figure 3:
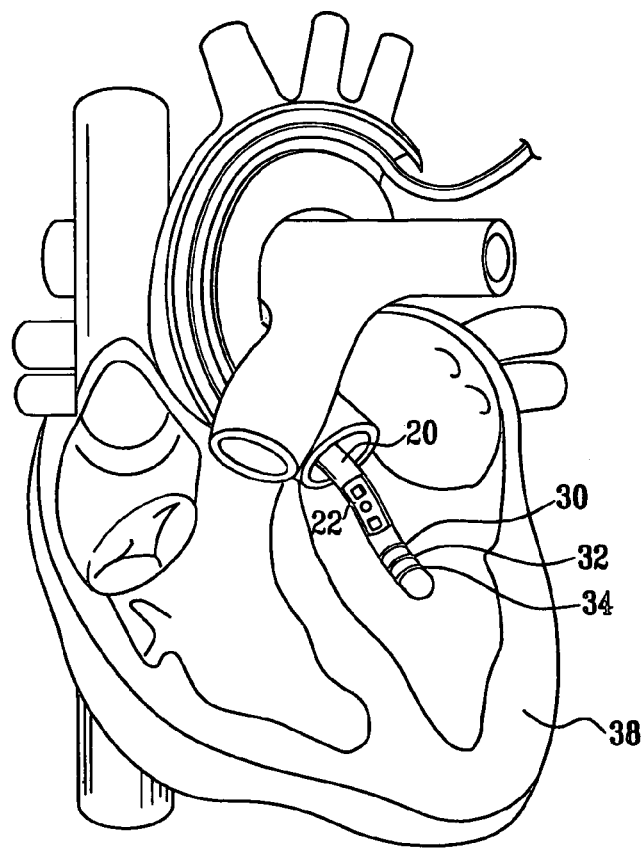
FIG. 3 is a schematic, pictorial cutaway view of a hybrid catheter within a heart chamber, where it is being used to generate a calibration map, in accordance with an embodiment of the present invention.

FIG. 3 is a schematic, pictorial illustration of hybrid catheter 20 positioned within a chamber of heart 38 during generation of a calibration map, in accordance with an embodiment of the present invention. The signals received from magnetic field sensor 22 are used to compute the position and orientation of the catheter at multiple locations, and, in particular, to derive the position coordinates of electrodes 30, 32, and 34 at these locations based on the magnetic coordinate measurements and the known displacement of the electrodes relative to sensor 22. Impedance measurements are also made to electrodes 30, 32, and 34 at the different catheter locations, and these measurements are correlated with the electrode positions as determined by the magnetic position measurements. In this manner a calibration map is generated.

Figure 4:
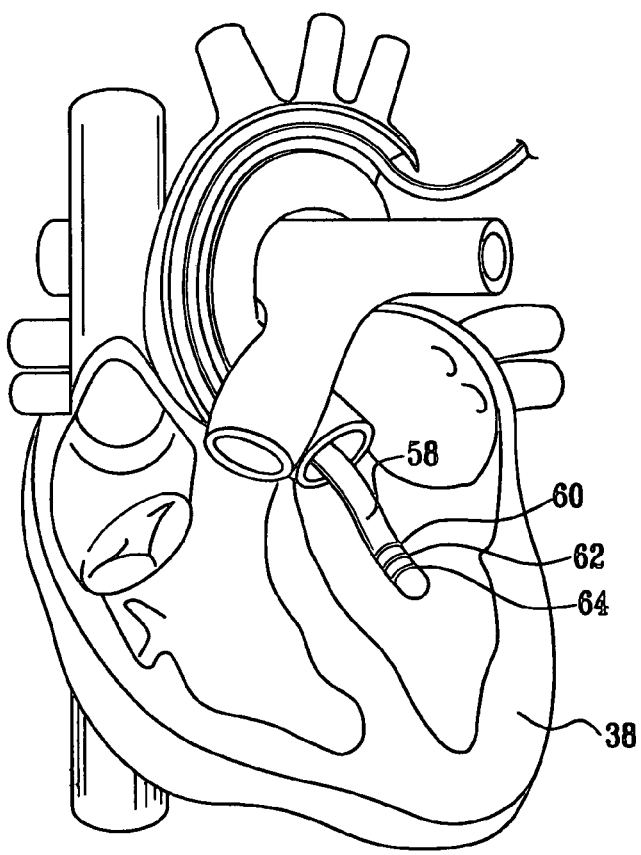
FIG. 4 is a schematic, pictorial cutaway view of a second catheter positioned in the heart chamber following calibration mapping, in accordance with an embodiment of the present invention.

FIG. 4 is a schematic, pictorial illustration of a second catheter 58, which is inserted into heart 38 during or after generation of the calibration map, in accordance with an embodiment of the present invention. As catheter 58 is moved through the heart chamber, impedance measurements taken at electrodes 60, 62, and 64 on the catheter are correlated with the impedance measurements that were previously recorded at known positions on the calibration map. In this manner, the coordinates of catheter 58 are determined accurately, notwithstanding the fluctuations and nonlinearities in the impedance of the subject's body.

Figure 5:
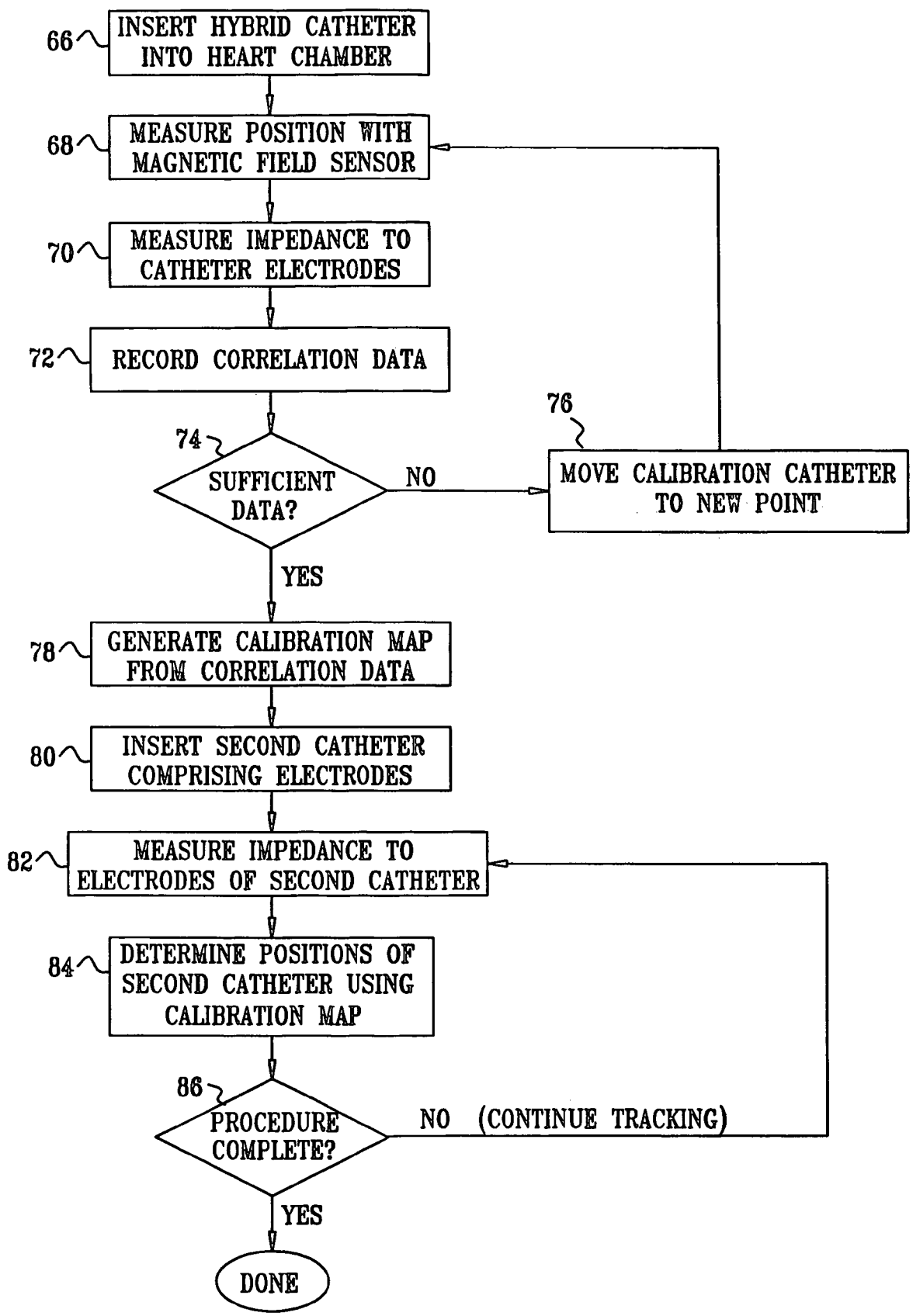
FIG. 5 is a flowchart that schematically illustrates a method for generating and applying a calibration map, in accordance with an embodiment of the present invention.

FIG. 5 is a flowchart showing a method for generating and applying a calibration map, as illustrated in FIGS. 3 and 4, in accordance with an embodiment of the present invention. In an initial step 66, a hybrid catheter, such as catheter 20, is inserted into a chamber of the heart (or into another body cavity, as appropriate). In a magnetic measurement step 68, the magnetic field sensor is used to determine the position coordinates of the catheter, and thus find the specific locations of the catheter electrodes. Impedance measurements at these catheter electrodes are then taken in an impedance measurement step 70. Next, in a correlation step 72, the impedance measurements are correlated with the electrode positions determined in step 68.

In a decision step 74, a determination is made as to whether sufficient data for a calibration map has been collected, based on the needs of the subsequent procedure. If more data is required, the hybrid catheter is moved to a new position in the heart chamber, at a positioning step 76, and steps 68 through 74 are repeated. In practice, steps 68 and 70 are performed continuously, so that steps 66 through 76 may be carried out in a continuous process, as well, while moving the catheter gradually through different parts of the cavity that is to be mapped.

Once sufficient data has been collected, a calibration map is generated in a mapping step 78. Typically, the calibration map comprises a grid of coordinates, determined by magnetic sensing, with a set of impedance measurements (relative to each of the body-surface electrodes or to pairs of body-surface electrodes) recorded at each point in the grid. Alternatively, the grid may be inverted, so that the map indicates the actual, calibrated position coordinates for each set of impedance measurements.

After the calibration map is complete, catheter 58, and/or another invasive medical device, is inserted into the body cavity, in an insertion step 80. The second catheter comprises electrodes that may be used to measure impedances, but it typically lacks magnetic field sensors. In a second impedance measurement step 82, impedances between the electrodes of the second catheter and the body-surface electrodes are measured. In a position sensing step 84, the position coordinates of these catheter electrodes are determined by comparing the measured impedances with the calibration map. Based on the electrode positions, the positions of other elements of the second catheter may also be determined.

As shown in FIG. 5, steps 82 and 84 may be repeated to continuously track catheter 58, until it is determined that the procedure is done, in a completion step 86.

FIGS. 6A-6D are pictorial illustrations of a hybrid catheter 88, in accordance with another embodiment of the present invention. Hybrid catheter 88 comprises a relatively rigid base section 90 extending to an inflection point 96, and further comprises a deformable flexible section 92 beyond point 96. As shown in FIG. 6A and FIG. 6B, Section 92 is of a known, fixed length, and comprises material that typically is twistable but not stretchable when subjected to pressure within the body cavity. Typically, section 92 is sufficiently resilient so as to assume a predetermined form when no force is applied thereto, and to be deflected from the predetermined form when a force is applied.

In the embodiment shown in FIG. 6A and FIG. 6C hybrid catheter 88 has a lasso shape, which is appropriate for circumferentially mapping and ablating the area around the ostium of a pulmonary vein in the left atrium. A catheter of this sort is described, for example, in U.S. patent application Ser. No. 10/629,661, filed Jul. 29, 2003, entitled "Lasso for Pulmonary Vein Mapping and Ablation," which is assigned to the assignee of the present invention and which is incorporated herein by reference. Alternatively, the aspects of the present invention that are described with reference to this catheter may also be applied to deflectable catheters of other sorts, such as basket catheters.

A magnetic sensor 94 is affixed to rigid section 90 of catheter 88 near point 96. One or more electrodes 98 are placed on flexible section 92 of the catheter. Electrodes 98 are adapted for measuring impedances as described above. In addition, some or all of electrodes 98 may also be adapted to perform additional functions, such as sensing electrical characteristics of body tissue, or performing ablation.

When catheter 88 is held in an initial position wherein no external forces are applied, position measurements made by magnetic sensor 94 may be used to determine the position of the entire catheter length, including the respective positions of electrodes 98. In this initial position, impedance measurements are also taken at the electrodes, in order to calibration the impedance measurements.

When a force is applied to flexible section 92, the section is deformed, thereby deflecting the electrodes from their calibrated positions. Because the deflection of each electrode is relatively small, impedance measurements may be used to determine relatively accurately the amount by which each electrode moved from its initial position. The position of each electrode, and hence the shape of catheter 88, can thus be determined accurately, even though only one magnetic field sensor is used.

System 36 represents an embodiment of the invention as it may be used in a catheter-based procedure for diagnosis or treatment of conditions of the heart, such as arrhythmias. System 36 can be used, as well, in the diagnosis or treatment of intravascular ailments, which may involve angioplasty or atherectomy. The principles of system 36 may also be applied, mutatis mutandis, in position-sensing systems for the diagnosis and/or treatment of other body structures, such as the brain, spine, skeletal joints, urinary bladder, gastrointestinal tract, prostrate, and uterus.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for position sensing, comprising:
    introducing a probe comprising a magnetic field transducer and at least one probe electrode into a body cavity of a subject;
    measuring position coordinates of the probe at a location in the body cavity using the magnetic field transducer;

measuring an impedance between the at least one probe electrode and one or more points on a body surface of the subject; and calibrating the measured impedance using the measured position coordinates.

2. The method according to claim 1, wherein the magnetic field transducer comprises one or more coils.

3. The method according to claim 1, wherein measuring the position coordinates of the probe comprises generating an external magnetic field and measuring signals induced in the magnetic field transducer due to the external magnetic field.

4. The method according to claim 1, wherein measuring the position coordinates comprises driving the magnetic field transducer to generate a magnetic field and measuring signals induced in an external magnetic field sensor due to the magnetic field.

5. The method according to claim 1, wherein measuring the impedance comprises driving an electrical current through the body between the at least one probe electrode and one or more body surface electrodes and measuring the impedance responsively to the current.

6. The method according to claim 5, wherein driving the electrical current through the body comprises maintaining a constant voltage between the at least one probe electrode and the one or more body surface electrodes, and wherein measuring the impedance comprises measuring the current at the constant voltage.

7. The method according to claim 5, wherein driving the electrical current through the body comprises maintaining a constant current between the at least one probe electrode and the one or more body surface electrodes, and wherein measuring the impedance comprises measuring a voltage between the at least one probe electrode and the one or more body surface electrodes.

8. The method according to claim 1, wherein measuring the impedance comprises applying a voltage across at least one pair of body surface electrodes and measuring a voltage drop at the at least one probe electrode.

9. The method according to claim 1, wherein measuring the position coordinates comprises determining the position coordinates using the magnetic transducer at a plurality of locations in the body cavity, and wherein measuring the impedance comprises determining the impedance at the plurality of the locations, and wherein calibrating the measured impedance comprises generating a calibration map using the position coordinates and the impedance determined at the plurality of the locations.

10. The method according to claim 9, wherein the probe used to generate the calibration map is a first probe, and wherein the method further comprises:

introducing into the body cavity a second probe comprising at least one second probe electrode, and measuring the impedance between the at least one second probe electrode and the one or more points on the body surface, and determining second position coordinates of the second probe by calibrating the impedance measured with respect to the second probe electrode using the calibration map.

11. The method according to claim 1, wherein the probe comprises a base section, where the magnetic field transducer is located, and a deformable section, where the at least one probe electrode is located, the deformable section having a known shape when undeformed, and wherein the calibrating the measured impedance comprises determining a deflection of the deformable section relative to the base section.

12. The method according to claim 11, wherein determining the displacement comprises measuring a first impedance when the deformable section is undeformed, and measuring a second impedance when the deformable section is deflected, and comparing the second impedance to the first impedance in order to determine the deflection.

13. A position sensing system, comprising:

a probe comprising a magnetic field transducer and at least one probe electrode and adapted to be introduced into a body cavity of a subject; and a control unit configured to measure position coordinates of the probe using the magnetic field transducer, and to measure an impedance between the at least one probe electrode and one or more points on a body surface of the subject, and to calibrate the measured impedance using the measured position coordinates.

14. The system according to claim 13, wherein the magnetic field transducer comprises one or more coils.

15. The system according to claim 13, and comprising an external magnetic field generator adapted to generate an external magnetic field, which causes the magnetic field transducer to generate a position signal, wherein the control unit is configured to receive and process the position signal so as to measure the position coordinates of the probe.

16. The system according to claim 13, wherein the magnetic field transducer is adapted to generate a magnetic field, and wherein the system further comprises an external magnetic field sensor adapted, responsively to the magnetic field, to generate a position signal, and wherein the control unit is configured to receive and process the position signal so as to measure the position coordinates of the probe.

17. The system according to claim 13, wherein the control unit is configured to drive an electrical current between the at least one probe electrode and body surface electrodes at the one or more points, and to measure the impedance responsively to the current.

18. The system according to claim 17, wherein the control unit is configured to maintain a constant voltage between the at least one probe electrode and the body surface electrodes, and to measure the current at the constant voltage.

19. The system according to claim 17, wherein the control unit is configured to maintain a constant current between the at least one probe electrode and the body surface electrodes, and to measure the voltage between the at least one probe electrode and the body surface electrodes.

20. The system according to claim 13, wherein the control unit is configured to apply a voltage across at least one pair of body surface electrodes at the one or more points and to measure the impedance by sensing a voltage drop at the at least one probe electrode.

21. The system according to claim 13, wherein the control unit is configured to determine the position coordinates using the magnetic transducer at a plurality of locations in the body cavity and to determine the impedance at the plurality of the locations, and to generate a calibration map determining the impedance at the plurality of the locations.

22. The system according to claim 21, wherein the probe used to generate the calibration map is a first probe, and wherein the system further comprises a second probe, comprising at least one second probe electrode and adapted to be introduced into the body cavity, and wherein the control unit is configured to measure the impedance between at least one second probe electrode and the one or more points on the body surface and to determine second position coordinates of the second probe by calibrating the impedance measured with respect to the second probe electrode using the calibration map.

23. The system according to claim 13, wherein the probe comprises a deformable section where the at least one probe electrode is located, and a base section, where the magnetic field transducer is located, the deformable section having a known shape when undeformed, and wherein the control unit is configured to calibrate the measured impedance so as to determine a deflection of the deformable section relative to the base section.

24. The system according to claim 23, wherein the control unit is configured to measure a first impedance when the deformable section is undeformed, and to measure a second impedance when the deformable section is deflected, and to compare the second impedance to the first impedance so as to determine the deflection of the probe.

* * * * *